US005585472A

United States Patent [19]
Wolf et al.

[11] Patent Number: 5,585,472
[45] Date of Patent: Dec. 17, 1996

[54] PREPARATION OF ALKYL GLYCOSIDES

[75] Inventors: Gerhard Wolf, Mannheim; Helmut Wolf, Hassloch, both of Germany

[73] Assignee: BASF Aktiengesellschaft, Ludwigshafen, Germany

[21] Appl. No.: 374,529

[22] PCT Filed: Aug. 12, 1993

[86] PCT No.: PCT/EP93/02131

§ 371 Date: Feb. 1, 1995

§ 102(e) Date: Feb. 1, 1995

[87] PCT Pub. No.: WO94/04544

PCT Pub. Date: Mar. 3, 1994

[30] Foreign Application Priority Data

Aug. 21, 1992 [DE] Germany ............ 42 27 752.3

[51] Int. Cl.⁶ ............ C07G 3/00; C07H 15/00; C07H 17/00
[52] U.S. Cl. .................... 536/18.6; 536/123.13; 536/124
[58] Field of Search .................. 536/18.6, 124, 536/123.13

[56] References Cited

U.S. PATENT DOCUMENTS

| | | | |
|---|---|---|---|
| 3,598,865 | 8/1971 | Lew | 536/4.1 |
| 3,839,318 | 10/1974 | Mansfield | 536/18.6 |
| 4,898,934 | 2/1990 | Leuders et al. | 536/18.6 |
| 4,963,534 | 10/1990 | Calabria et al. | 514/54 |
| 4,977,254 | 12/1990 | Homer et al. | 536/124 |
| 5,124,446 | 6/1992 | Grüning et al. | 536/120 |
| 5,166,337 | 11/1992 | Ripke | 536/126 |
| 5,206,357 | 4/1993 | Schmidt | 536/18.6 |
| 5,266,690 | 11/1993 | McCurry et al. | 536/18.6 |
| 5,268,461 | 12/1993 | Shoji et al. | 536/41 |
| 5,374,716 | 12/1994 | Biermann et al. | 536/18.6 |

FOREIGN PATENT DOCUMENTS

| | | |
|---|---|---|
| 0132043 | 1/1985 | European Pat. Off. . |
| 0415192 | 3/1991 | European Pat. Off. . |
| 0453238 | 10/1991 | European Pat. Off. . |
| 0279482 | 6/1990 | Germany . |
| 4006192 | 2/1991 | Germany . |
| 2221462 | 2/1990 | United Kingdom . |
| 9007516 | 7/1990 | WIPO . |
| 9109923 | 7/1991 | WIPO . |
| 9115193 | 10/1991 | WIPO . |
| 9115192 | 10/1991 | WIPO . |
| 9320171 | 10/1993 | WIPO . |
| 9505796 | 3/1995 | WIPO . |

OTHER PUBLICATIONS

Gokel et la., "Phase Transfer Catalysis–Part I: General Principles," *J. Chem. Ed.*, 55(6), 350–354 (1978).
Dehmlow, "Phasentransfer–Katalyse. Eine Vielseitige, Modern Synthesetechnik mit Potential Bedeutung für die Farbenchemie," *Chimica*, 34(1), 12–20(1980).
"Phase Transfer Catalysis," *Eastman Organic Chemical Bulletin, 48(1), 1–3, (1976).*

Primary Examiner—John Kight
Assistant Examiner—L. Eric Crane
Attorney, Agent, or Firm—Oblon, Spivak, McClelland, Maier & Neustadt, P.C.

[57] ABSTRACT

Alkyl glycosides are prepared by reacting alcohols with monosaccharides or compounds which, under the reaction conditions, form monosaccharides, in the presence of amphoteric surfactants in the acid form as catalysts, and subsequently neutralizing the reaction mixture with bases.

4 Claims, No Drawings

PREPARATION OF ALKYL GLYCOSIDES

The present invention relates to a process for preparing alkyl glycosides by reacting alcohols with monosaccharides or compounds which, under the reaction conditions, form monosaccharides, in the presence of acid catalysts, and subsequently neutralizing the reaction mixture with bases.

Surface-active alkyl glycosides, which are mainly used for detergents and cleaners, have been known for a long time. They are prepared on the industrial scale by two different processes, either by direct synthesis in which the long-chain alcohol component is directly linked to the sugar component with elimination of water, or by the transacetalization method in which a short-chain alkyl glycoside is initially prepared and then, in a second stage, reacted with long-chain alcohols to give the surface-active alkyl glycoside. Acid catalysts are required for both processes. Thus, for example, U.S. Pat. No. 3 598 865 discloses the use of sulfuric acid, hydrochloric acid, phosphoric acid, phosphorous acid, toluenesulfonic acid or boron trifluoride as catalyst. As is evident from U.S. Pat. No. 3 839 318, direct reaction of saccharides and long-chain alcohols can also be carried out in the presence of acid ion exchangers. EP-B-132 043 discloses the use of anionic surfactants in the acid form as catalyst for preparing alkyl glycosides. DE-A-3 927 919 discloses the use of sulfosuccinic acid as catalyst in the preparation of alkyl glycosides. WO-A-90/07 516 discloses the use of dialkylnaphthalenesulfonic acids as catalyst in the preparation of alkyl glycosides. The abovementioned catalysts have various disadvantages. In particular, sulfuric acid and phosphoric acid lead to the formation of polysaccharides during the reaction of the alcohols with monosaccharides. In addition, the products obtained on use of these catalysts are highly colored. Other catalysts, such as anionic surfactants in the acid form, eg. dodecylbenzenesulfonic acid, likewise yield alkyl glycosides with relatively high color numbers.

It is an object of the present invention to provide a process for preparing alkyl glycosides in which the formation of polyglycosides from the monosaccharides is greatly reduced and in which the reaction products have a very low iodine number.

We have found that this object is achieved by a process for preparing alkyl glycosides by reacting alcohols with monosaccharides or compounds which, under the reaction conditions, form monosaccharides, in the presence of acid catalysts, and subsequently neutralizing the reaction mixture with bases, wherein amphoteric surfactants in the acid form are employed as catalysts. Amphoteric surfactants which are particularly preferably used are quaternary eminoalkylsulfonates, quaternary aminoalkyl sulfates or mixtures thereof.

In the literature, the emphoteric surfactants are also called sulfo betaines or sulfato betaines. They can also be employed in the form of the alkali metal or ammonium salts as catalyst. However, in this case it is necessary to liberate the free acid therefrom by adding a strong acid, eg. sulfuric acid or hydrochloric acid. The liberation of the acid can be carried out separately from the preparation of the alkyl glycosides or else take place in the reaction medium itself.

The amphoteric surfactants in the acid form are suitable for preparing all alkyl glycosides disclosed to date. The alkyl glycosides may be described by the formula $RO(G)_m$ where G is a saccharide unit, m is from 1 to 12, preferably 1 to 4, and R is an aliphatic radical with 1 to 30 carbons.

The saccharide unit G may comprise the customary aldoses and ketoses, eg. glucose, fructose, mannose, galactose, talose, gulose, allose, altrose, idose, arabinose, xylose, lyxose and ribose. Also possible are saccharide mixtures, oligosaccharides, eg. maltose, lactose and palatinose, or mixtures of mono- and oligosaccharides. The saccharides can be employed both in anhydrous form and with water of crystallization or else as aqueous syrup. The use of an aqueous saccharide syrup is preferred for economic reasons. The water content of the aqueous saccharide syrup is from 10 to 80, preferably from 15 to 60, % by weight. Industrial solutions with water contents of 20–40% by weight are preferably used. The saccharide preferably used is an aqueous glucose syrup or glucose.

Compounds which form monosaccharides under the reaction conditions are oligo- and polysaccharides. $C_1$–$C_5$-alkyl glycosides which are transacetalized with $C_6$–$C_{30}$ alcohols can also be regarded as compounds which form monosaccharides under the reaction conditions.

The alcohols used to form the alkylglycosides can have any desired chain length from $C_1$ to $C_{30}$. Primary aliphatic alcohols are preferably employed. To prepare surface-active glycosides which are employed as surfactant raw materials in detergents and cleaners, preferably primary aliphatic alcohols with from 6 to 20, in particular with from 8 to 16, carbons are reacted with monosaccharides or compounds which form monosaccharides under the reaction conditions. The higher aliphatic alcohols are prepared, for example, from industrial fats. However, it is, of course, also possible to employ synthetic primary alcohols, eg. oxo alcohols, as reaction component. Diols can also be employed as alcohol component, eg. ethylene glycol, proylene glycols, butanediols such as 1,4-butanediol and hexanediols, especially 1,6-hexanediol. Diols which can also be used are 1,2- and 1,3-alkanediols with the structures

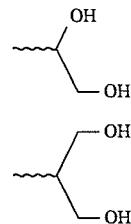

Hydroxyalkyl glycosides are obtained when diols are used.

The higher aliphatic primary $C_8$–$C_{18}$ alcohols which are preferred are preferably saturated and, in particular, straight-chain alcohols which are prepared by hydrogenation of natural fatty acids on the industrial scale. Typical examples of the higher aliphatic alcohols are n-dodecyl alcohol, n-tetradecyl alcohol, n-hexadecyl alcohol, n-octadecyl alcohol, n-octyl alcohol, decyl alcohol, undecyl alcohol and tridecyl alcohol. Since the fatty alcohols are preferably prepared from natural fats; they normally take the form of technical mixtures, which are also employed to prepare the alkyl glycosides. Apart from the fatty alcohols obtained from natural fats, also suitable for the reaction are branched primary alcohols, for example oxo alcohols. Typical examples of oxo alcohols are $C_{12}/C_{13}$ alkanols with about 25% methyl branching, mainly in position 2 (Dobanol 23), and the corresponding $C_9$–$C_{11}$ alcohols (Dobanol 91). However, the alcohols obtainable from natural fats are preferably used.

The reaction of the alcohols with the monosaccharides or compounds which form monosaccharides under the reaction conditions takes place according to the invention in the presence of amphoteric surfactants in the acid form. Alkyl glycosides of the formula $RO(G)_m$ where G and R have the abovementioned meanings, and m is from 1 to 12, are obtained. The value of m should be as small as possible because the alkyl polyglycosides which are produced in minor amounts in the reaction have less detergent power than the alkyl monoglycosides. The value of m is therefore preferably from 1.1 to 1.5. The alkyl glycosides produced in the reaction are mixtures of alkyl mono- and oligoglycosides. It is therefore also possible for m not to be a whole number. Besides the alkyl glycosides, it is also possible for unwanted polysaccharides of various composition to be formed by polymerization of the saccharides. However, this reaction is substantially suppressed when the amphoteric surfactants in the acid form are used according to the invention.

Examples of amphoteric surfactants in the acid form are:

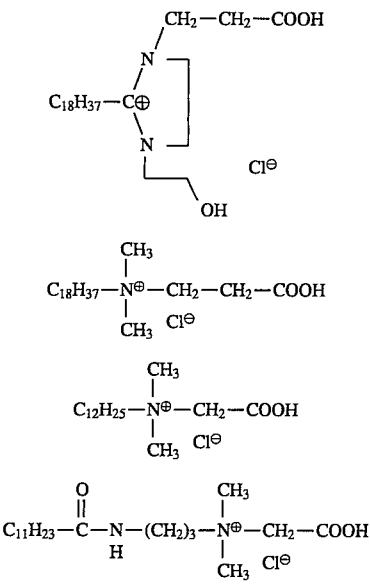

Quaternary aminoalkylsulfonates and quaternary aminoalkyl sulfates in the acid form can be described, for example, by the following formulae:

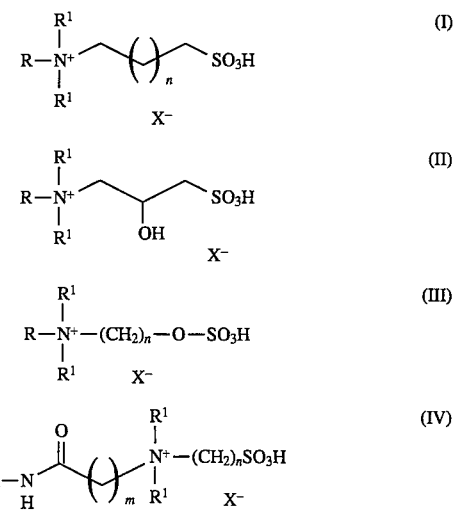

In the formulae I to IV, R is $C_8$–$C_{30}$-alkyl, $R^1$ is $C_1$–$C_{20}$-alkyl and X is an anion, preferably $HSO_4^-$, $SO_4^{2-}$ and $Cl^-$. The value of n is 0–10 in formula I and 2–10 in each of formulae III and IV. The value of m in formula IV is 1–6.

Examples of compounds of the formula I are dimethyl (3-sulfopropyl)stearylammonium chloride and dimethyl (3-sulfopropyl)laurylammonium chloride.

Examples of suitable compounds of the formula II are dimethyl (2-hydroxy-3-sulfopropyl)laurylammonium chloride and dimethyl(2-hydroxy-3-sulfopropyl)stearylammonium chloride.

Examples of suitable compounds of the formula III are dimethyl(3-hydroxysulfonyloxypropyl)laurylammonium chloride and dimethyl(3-hydroxysulfonyloxypropyl)-stearylammonium chloride.

An example of compounds of the formula IV is dimethyl (3-sulfopropyl)-3-stearylcarbamoylpropylammonium chloride.

The compounds of the formulae I to IV indicated above can be employed not only in the acid form but also in the form of the sulfonic acid salts as catalyst in the preparation of alkyl glycosides. However, it is then necessary for the amphoteric surfactants to be in the acid form produced by addition of strong acids such as sulfuric acid or hydrochloric acid to their salts. The liberation of the free acids of the amphoteric surfactants from the salts can also take place in the reaction medium.

The process according to the invention is preferably used to prepare alkyl glycosides from alcohols with from 6 to 30 carbons. Based on the monosaccharides employed in the reaction, the amphoteric surfactants in the acid form are used in amounts of from 0.1 to 5, preferably 0.1 to 0.5, mol %. The amounts of amphoteric surfactants in the acid form normally employed as catalysts are less than the amounts of catalysts otherwise used. The direct reaction of glucose syrups with long-chain alcohols can be carried out without the emulsifiers which are normally added. The alkyl glycosides which are prepared using amphoteric surfactants in the acid form have a paler color than alkyl glycosides prepared with other catalysts. In addition, less bleach is needed to bleach the glycosides obtained by the process according to the invention than for alkyl glycosides obtained by known processes.

The percentages in the examples are by weight.
The following catalysts were used in the examples:
Catalyst 1: Dimethyl(3-sulfopropyl)laurylammonium betaine (RALUFON DL), protonated with sulfuric acid
Catalyst 2: Coconut fatty dimethyl(3-sulfopropyl)ammonium betaine (RALUFON DCH), protonated with sulfuric acid
Catalyst 3: Dimethyl(3-sulfopropyl)stearylammonium betaine (RALUFON DS), protonated with sulfuric acid.

The following catalysts were tested for comparison with the prior art:
Catalyst 4: Dodecylbenzenesulfonic acid
Catalyst 5: p-Toluenesulfonic acid
Catalyst 6: Sulfuric acid.

EXAMPLE 1a)

1033 g of a $C_8$–$C_{10}$ fatty alcohol mixture (Lorol 810 S) were introduced into a 2 l multi-neck flask equipped with stirrer, baffles, thermometer, distillation head and a metering unit comprising a metering pump, a pressure-maintaining valve and a nozzle, and 3 g of dimethyl (3-sulfopropyl)laurylammonium betains (Ralufon DL) and 0.46 g of 96% strength sulfuric acid were added. The amount of amphoteric surfactant in the form of the sodium salt was 0.5 mol % based on glucose. This mixture was mixed with 21 g of a $C_8/C_{10}$-alkyl glucoside/$C_8$–$C_{10}$ fatty alcohol mixture as emulsifier. The emulsifier mixture contained about 65% alcohols and about 35% glucose. The solution was heated to 115°–120° C., and the pressure was adjusted to from 50 to 60 mbar. Then 485 g of a glucose syrup (65% strength aqueous solution) preheated to 60° C. were added continuously. At the same time, the water introduced with the glucose syrup into the system was removed by distillation. After a metering time of 4 hours, the reaction mixture was then maintained at about 120° C. for 30 minutes. The result was a slightly cloudy, pale yellow reaction solution which was cooled and then neutralized with 50% strength aqueous sodium hydroxide solution. The excess alcohol was then removed by distillation, and the residue was converted into a 60% strength aqueous solution, which was bleached with 6 g of 30% strength hydrogen peroxide solution at 80° C. The iodine color number of the bleached reaction solution was 5.

EXAMPLES 1b) AND 1c), AND COMPARATIVE EXAMPLES 1–3

Example 1a) was repeated with the catalysts shown in Table 1. The results obtained with these are indicated in Table 1, specifically the amount of polyglucose in the reaction mixture, the hydrogen peroxide used to bleach the reaction mixture, and the color number of the bleached reaction mixture.

TABLE 1

| Example 1 | Catalyst No. | Polyglucose [%] in the reaction mixture | $H_2O_2$ used [g] | Iodine color No. of the bleached reaction mixture |
|---|---|---|---|---|
| a) | 1 | 6 | 6.0 | 5 |
| b) | 2 | 8 | 6.0 | 7.5 |
| c) | 3 | 4 | 4.5 | 4 |
| Comparative Examples | | | | |
| 1 | 4 | 4 | 6.0 | 10 |
| 2 | 5 | 18 | 9.0 | 18.5 |
| 3 | 6 | 25 | 12.0 | 25 |

EXAMPLE 2 a) Example 1a) was repeated with catalyst 3.

b) Example 1a) was repeated but with omission of the emulsifier and use of catalyst 3 in place of catalyst 1. The results are indicated in Table 2.

COMPARATIVE EXAMPLE 4

Example 1a) was repeated but with catalyst 4 in place of the catalyst used there.

COMPARATIVE EXAMPLE 5

Example 1a) was repeated but with omission of the emulsifier described in Example 1a) and using the catalyst 4 in place of the catalyst described there. The results are indicated in Table 2.

TABLE 2

| Example 1 | Catalyst No. | Polyglucose [%] in the reaction mixture | $H_2O_2$ used [g] | Iodine color No. of the bleached reaction mixture |
|---|---|---|---|---|
| a | 3 | 4 | 4.5 | 4 |
| b | 6 | 6.0 | 8 | |
| Comparative Examples | | | | |
| 4 | 5 | 9 | 6.0 | 10 |
| 5 | 4 | ** | 10.0 | 12 |

** Heavy precipitate after the metering phase, composed of about 80–90% polyglucose

EXAMPLE 3 a) Example 1a) was repeated with catalyst 3. The catalyst concentration was 0.5 mol % based on glucose. The results are indicated in Table 3.

b) Example 1a) was repeated by using, in place of the catalyst employed there, catalyst 3 in an amount of 0.1 mol % based on glucose. The results are indicated in Table 3.

COMPARATIVE EXAMPLE 6

Example 1 was repeated but employing catalyst 4 in a concentration of 0.1 mol % based on glucose. The results are indicated in Table 3.

TABLE 3

| Example 3 | Catalyst No. | Cat. conc. [mol % based on glucose] | Polyglucose [%] in the reaction mixture | Residue after metering phase |
|---|---|---|---|---|
| a | 13 | 0.5 | 4 | none |
| b | 13 | 0.1 | 4 | none |
| Comparative Example 6 | 4 | 0.1 | 12 | 29 g |

We claim:

1. A process for preparing alkyl glycosides by reacting alcohols with monosaccharides or compounds which, under the reaction conditions, form monosaccharides, in the presence of acid catalysts, and subsequently neutralizing the reaction mixture with bases, wherein amphoteric surfactants in the acid form are employed as catalysts.

2. A process as claimed in claim 1, wherein quaternary aminoalkylsulfonates, quaternary aminoalkyl sulfates or mixtures thereof are employed as amphoteric surfactant.

3. A process as claimed in claim 1 or 2, wherein alcohols with from 8 to 30 carbons are employed.

4. A process as claimed in claim 1 or 2, wherein the amphoteric surfactants are employed in amounts of from 0.1 to 5 mol % based on monosaccharides.

* * * * *